United States Patent [19]
Takagaki et al.

[11] Patent Number: 5,068,364
[45] Date of Patent: Nov. 26, 1991

[54] CHALCONE DERIVATIVES AND PROCESS FOR PRODUCING THE SAME

[75] Inventors: Hidetsugu Takagaki; Shigenori Nakanishi, both of Sakura; Masayoshi Abe, Chiba; Hiromi Ohki; Yoshiyuki Sano, both of Sakura, all of Japan

[73] Assignee: Dainippon Ink and Chemicals, Inc., Tokyo, Japan

[21] Appl. No.: 439,435

[22] Filed: Nov. 21, 1989

[30] Foreign Application Priority Data

Nov. 21, 1988 [JP] Japan ................... 63-292436

[51] Int. Cl.$^5$ .......................... C07D 309/12
[52] U.S. Cl. .................... 549/415; 549/416
[58] Field of Search ............ 549/415, 416, 403; 568/334

[56] References Cited

U.S. PATENT DOCUMENTS 4,226,804 10/1980 Du Bois et al. .................. 549/403

FOREIGN PATENT DOCUMENTS 2506356 8/1975 Fed. Rep. of Germany ........ 562/42

OTHER PUBLICATIONS

Kamiya et al., C. A., 89:197,876g (1978).

Primary Examiner—Nicky Chan
Attorney, Agent, or Firm—Oblon, Spivak, McClelland, Maier & Neustadt

[57] ABSTRACT

Chalcone derivatives having at least one tetrahydropyranyloxy group is disclosed. Typically, the compounds are represented by general formula (I)

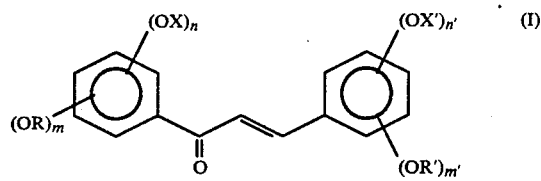

wherein X and X' each represent a tetrahydropyranyl group, R and R', which are then same or different, each represent an alkyl group or a hydrogen atom, n and n' each are an integer of from 0 to 5, m and m' each are integers of from 0 to 5, provided that $n+n'$ is 1 or more, and that $n+m$ is an integer of from 0 to 5 and $n'+m'$ is an integer of from 0 to 5. Also, disclosed are processes for producing the chalcone derivatives starting from acetophenone or its derivative and benzaldehyde or its derivative at least one of which has at least one tetrahydropyranyloxy group. Further, disclosed is 2,3,4,2',4'-pentahydroxychalcone.

18 Claims, No Drawings

CHALCONE DERIVATIVES AND PROCESS FOR PRODUCING THE SAME

BACKGROUND OF THE INVENTION

The present invention relates to novel chalcone derivatives, which are intermediates for the production of hydroxychalcones, and also to processes for producing hydroxychalcones using such chalcone derivatives.

Chalcone series compounds include chalcone, which can be produced by Claisen condensation reaction of acetophenone, and benzaldehyde and derivatives of chalcone. These chalcone compounds are known to have various pharmacological activities.

For example, Japanese Patent Application (Kokai) No. Sho 60-178815 describes examples in which chalcone compounds are used as active ingredients of antitumor drugs. Also, there is reported in Japanese Patent Publication (Kokoku) No. Sho 48-8485 that isoliquiritigenin (or 4,2',4'-trihydroxychalcone) is contained in extract of licorice root, exhibits antiulcer activity and is used in the therapy of gastric ulcer. Furthermore, it is known that isoliquiritigenin has antiallergic activity and is effective for the therapy, treatment and prophylaxis of asthma, allergic dermatitis, allergic rhinitis, urticaria, food allergy, and the like (Japanese Patent Application (Kokai) No. Sho 62-2027212). It is also known that isoliquiritigenin is also effective as a drug for the therapy, treatment and prophylaxis of kidney diseases such as kidney lesion caused by antitumor drugs, acute nephritis, chronic nephritis, Rehpus nephritis, and the like, and effective as a drug for the therapy, treatment and prophylaxis of liver diseases such as liver lesion caused by antitumor drugs, acute hepatitis, chronic hepatitis and the like (WO87-7835).

It is already known that isoliquiritigenin can be produced by reacting 2,4-dihydroxyacetophenone with 4-hydroxybenzaldehyde under alkaline conditions according to the following reaction scheme.

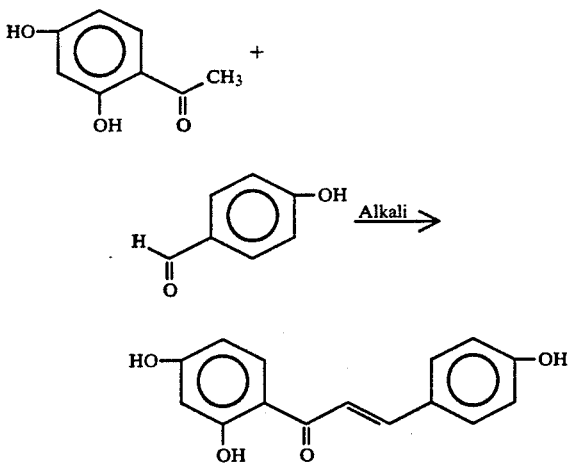

However, the yield of isoliquiritigenin obtained by the above reaction is about 20%, and in addition, chalcone compounds having a hydroxyl group at the 2-position of the acetophenone skeleton are obtained generally in low yield. Therefore, improvement for increasing the yield of chalcone compounds has been desired.

SUMMARY OF THE INVENTION

Therefore, the present invention provides a chalcone compound having at least one tetrahydropyranyloxy group in the chalcone skeleton.

The present invention also provides a process for producing a chalcone compound having at least one tetrahydropyranyloxy group.

Further, the present invention provides a novel hydroxychalcone derivative.

Also, the present invention provides a process for producing a hydroxychalcone by hydrolyzing a chalcone compound having at least one tetrahydropyranyloxy group in the chalcone skeleton.

The hydroxychalcone derivatives having at least one tetrahydropyranyloxy group are useful for producing hydroxychalcones which are useful as therapeutic agents.

According to the present invention, chalcone derivatives having at least one tetrahydropyranyloxy group can be obtained in high yield from starting compounds, and such chalcone derivatives can be decomposed with water or alcohols to release hydroxychalcones also in high yield, resulting in that the yield of hydroxychalcones can be increased as high as, e.g., 80% and about 4 times as high as the yield attained by direct synthesis of the hydroxychalcones using the corresponding starting compounds whose hydroxyl group(s) is or are not substituted with tetrahydropyranyloxy group. The present invention can provide process for producing chalcone derivatives at low cost, which assures easy obtention of intermediates for the production of hydroxychalcones and thus permits production of hydroxychalcones in high yield and at low cost.

DETAILED DESCRIPTION OF THE INVENTION

The novel chalcone derivatives having at least one tetrahydropyranyloxy group which the present invention provides, for example, those compounds in which at least one hydroxyl group in the hydroxychalcone is substituted with a tetrahydropyranyloxy group, include compounds represented by general formula (I) below.

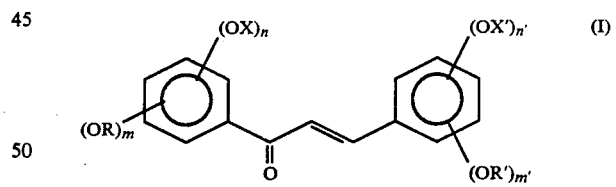

wherein X and X' each represent a tetrahydropyranyl group, R and R', which are the same or different, each represent an alkyl group or a hydrogen atom, n and n' each are an integer of from 0 to 5, m and m' each are integers of from 0 to 5, provided that n+n' is 1 or more, and that n+m is an integer of from 0 to 5 and n'+m' is an integer of from 0 to 5.

Preferred examples of the chalcone compounds are those in which n, n', m, and m' each are an integer of from 1 to 3, provided that n+m and n'+m' each are an integer of from 1 to 3. In this case, combinations of n and n' being an integer of from 1 to 3 and m and m' each being 0 may also be possible.

As specific compounds included in the above-described preferred examples, there can be cited, for example, the following compounds.

3,4,3'-Tris(tetrahydropyranyloxy)chalcone (I-1)

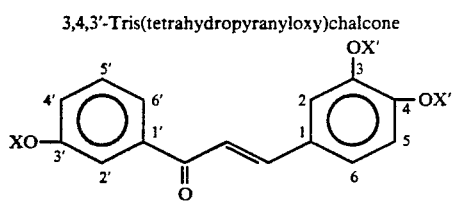

3,4,4'-Tris(tetrahydropyranyloxy)chalcone (I-2)

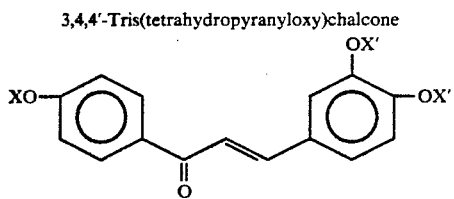

Also, compounds can be used which have a hydroxyl group at the 2-position of acetophenone skeleton and are represented by general formula (II) below.

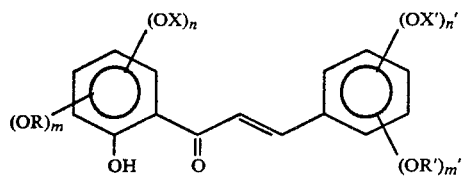
(II)

wherein X and X' each represent a tetrahydropyranyl group, R and R', which are the same or different, each represent an alkyl group or a hydrogen atom, n is an integer of from 0 to 2, n' is an integer of from 0 to 3, m is an integer of from 0 to 2, and m' is an integer of from 0 to 3, provided that $n+n'$ is 1 or more, and that $n+m$ is an integer of from 0 to 3 and $n'+m'$ is an integer of from 1 to 3.

Specific compounds embraced by general formula (II) include the following compounds.

2'-Hydroxy-3,4-bis(tetrahydropyranyloxy)chalcone (II-1)

2'-Hydroxy-4'-tetrahydropyranyloxychalcone (II-2)

2'-Hydroxy-4,4-bis(tetrahydropyranyloxy)chalcone (II-3)

2'-Hydroxy-3,4,4'-tris(tetrahydropyranyloxy)chalcone

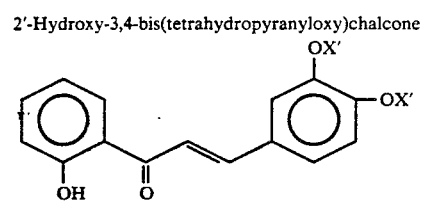
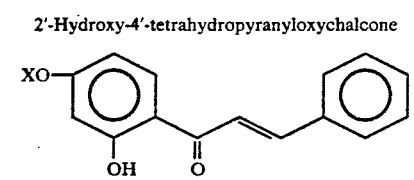
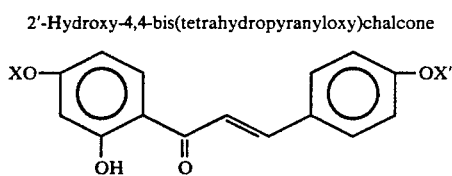
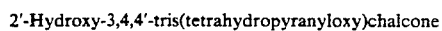

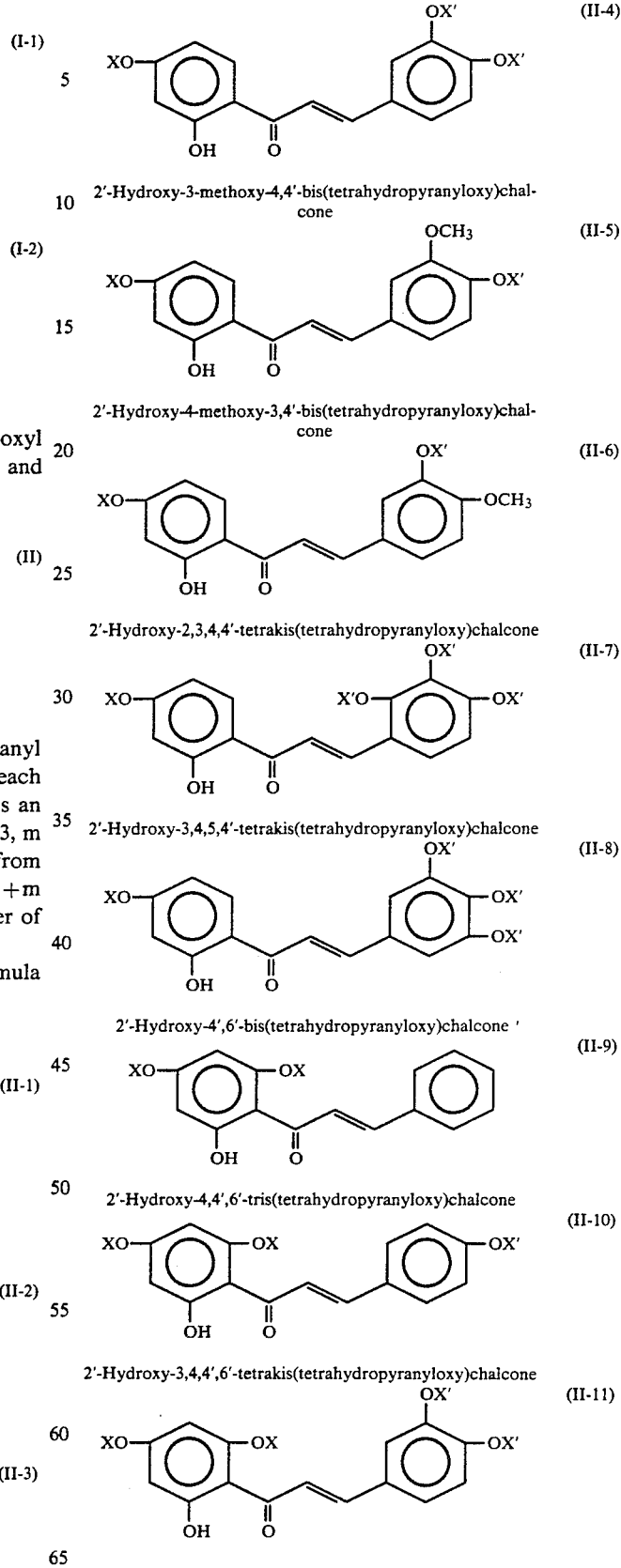

In the present invention, in order to produce chalcone derivatives having at least one tetrahydropyranyloxy group in the chalcone skeleton, acetophenone having at least one tetrahydropyranyloxy group or its derivative is reacted by Claisen condensation with benzaldehyde or its derivative, or alternatively acetophenone or its derivative is reacted by Claisen condensation with benzaldehyde having at least one tetrahydropyranyloxy group or its derivative. The tetrahydropyranyloxy group or groups is or are substituted with one or more hydroxyl groups, if any, attached to acetophenone (or its derivative) or benzaldehyde (or its derivative), thus increasing the yield of chalcone derivatives by Claisen condensation reaction.

The acetophenone having at least one tetrahydropyranyloxy group or its derivatives includes compounds represented by general formula (III) below

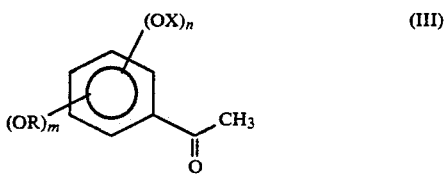

wherein X represents a tetrahydropyranyl group, R represents an alkyl group or a hydrogen atom, n and m each are an integer of from 0 to 5.

The benzaldehyde having at least one tetrahydropyranyloxy group or its derivatives include compounds represented by general formula (IV) below

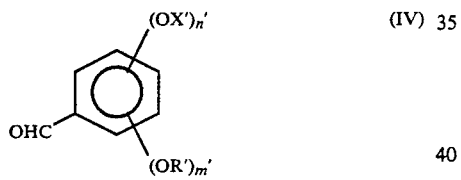

X' represents a tetrahydropyranyl group, R' is an alkyl group or a hydrogen atom, and n' and m' each are an integer of from 0 to 5.

In general formulae (III) and (IV), n and n' may be an integer of from 0 to 3, and m and m' may also be an integer of from 0 to 3.

The chalcone derivatives of the present invention represented by general formula (II) above can also be produced by using compounds represented by general formula (III') below

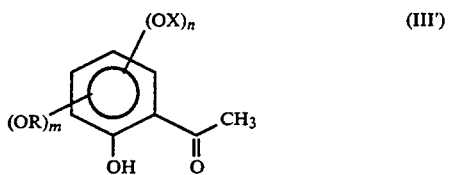

wherein X represents a tetrahydropyranyl group, R represents an alkyl group or a hydrogen atom, n is an integer of from 0 to 2, and m is an integer of from 0 to 3, and those represented by general formula (IV') below.

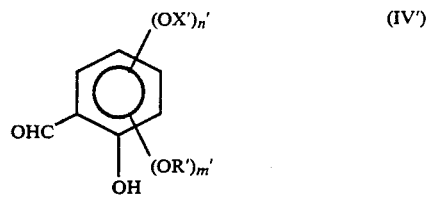

wherein X' represents a tetrahydropyranyl group, R' represents an alkyl group or a hydrogen atom, m' and n' each are an integer of from 0 to 3.

The acetophenone derivatives which have at least one tetrahydropyranyloxy group can be obtained, for example, by reacting acetophenone having one or more hydroxyl groups (OH) with dihydropyran in an organic solvent in the presence of an acid catalyst. For example, substitution of hydroxyl group at the 4-position of 2,4-dihydroxyacetophenone with a tetrahydropyranyloxy group proceeds as follows.

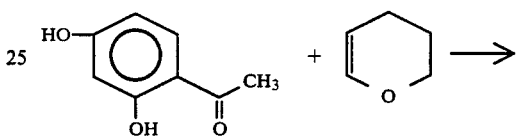

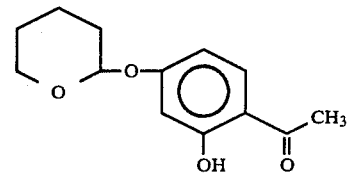

As for the acid catalyst, there can be cited mineral acids such as hydrochloric acid, sulfuric acid and the like, organic acids such as acetic acid, p-toluenesulfonic acid and the like, H+ type ion exchange resins, and salts thereof that are acidic, etc. For example, pyridinium p-toluenesulfonate is preferred when substituting, with tetrahydropyranyloxy group, one or more hydroxyl groups attached to those compounds having plural hydroxyl groups such as acetophenone or its derivative, or benzaldehyde or its derivative, having one or more hydroxyl groups in addition to the hydroxyl group at the respective 2-positions of these compounds.

As for the organic solvent, there can be used those other than alcohols, water, dimethylformamide and dimethyl sulfoxide. For example, aromatic and aliphatic hydrocarbons, ketones, esters, ethers, halogenated hydrocarbons, and the like can be used.

Generally, the reaction temperature and reaction time may vary depending on the kind and amount of the catalyst to be used as well as the kind of the solvent to be used. When the reaction is allowed to proceed in a solvent such as methylene chloride in the presence of a catalyst such as pyridinium p-toluenesulfonate, it is preferred that hydroxyacetophenone and the acid catalyst are charged in methylene chloride or the like solvent and dihydropyran is dropped at a temperature of from 0° to 40° C. in from 1 to 2 hours, followed by agitation for from 2 to 3 hours.

The reaction product is neutralized with a base such as caustic soda (sodium hydroxide), caustic potasse (potassium hydroxide), potassium carbonate, sodium bicarbonate, etc., and filtered, followed by concentration of the filtrate after removing excess amount of the base. The concentration is carried out preferably under reduced pressure. In this manner, acetophenone derivatives having one or more tetrahydropyranyloxy groups can be obtained as oily products.

The formation of them can be confirmed by various analytical methods such as infrared absorption spectrum (IR), nuclear magnetic resonance spectrum (NMR), mass spectrum, and the like.

The benzaldehyde compounds having at least one tetrahydropyranyloxy group can be produced and identified in a manner similar to that for the above-described acetophenone derivatives. For example, 4-hydroxybenzaldehyde can be produced as follows.

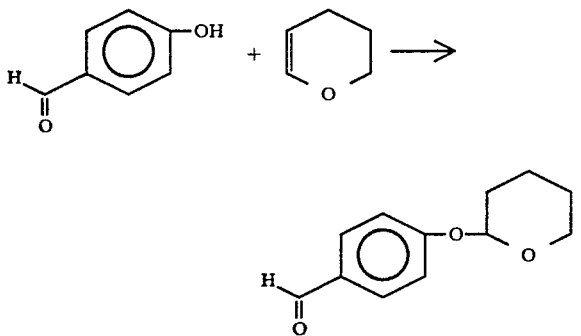

Although the acetophenone and benzaldehyde compounds each having at least one tetrahydropyranyloxy group may be produced separately as described above, one or more tetrahydropyranyloxy groups can be introduced in the skeletons of both acetophenone and benzaldehyde at the same time by mixing acetophenone having one or more hydroxyl groups with benzaldehyde having one or more hydroxyl groups, and then subjecting the mixture to a reaction for introducing tetrahydropyranyloxy groups as described above.

The reaction between acetophenone or its derivative and benzaldehyde or its derivative is performed by Claisen condensation reaction. It is preferred to use a basic catalyst, particularly hydroxides of alkaline earth metals. As for the hydroxides, there can be used, for example, hydroxides of magnesium, calcium, strontium, barium, or their hydrates. Of these, barium hydroxide and its hydrate is preferred. In this case, it is preferred to use as the solvent lower alcohols such as methanol, ethanol, isopropanol and n-propanol, water, and mixtures thereof.

Concretely, a reaction components such as acetophenone derivative and benzaldehyde derivative each having one or more tetrahydropyranyloxy groups are dissolved in a solvent together with the above-described catalyst, and the mixture is agitated at a temperature of from 30° to 60° C. for from 6 to 12 hours to perform Claisen condensation reaction. For example, when the above-described tetrahydropyranyloxylated acetophenone and benzaldehyde derivatives are used, the reaction proceeds as follows.

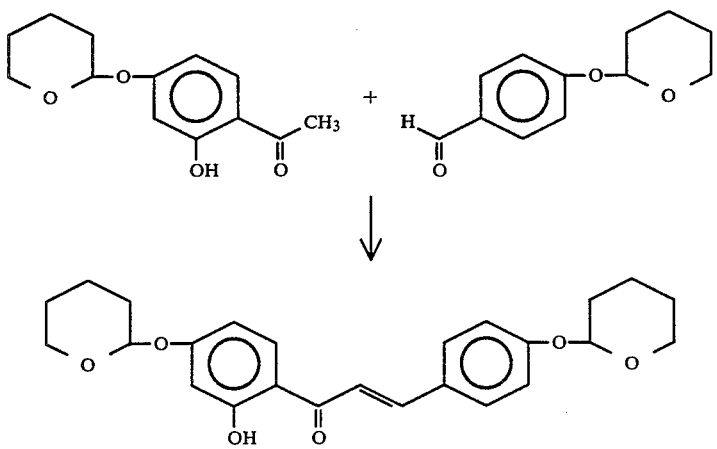

to obtain 2'-hydroxy-4,4'bis(tetrahydropyranyloxy)-chalcone.

The resulting mixture is cooled to room temperature and to this is added oil-soluble solvent such as methylene chloride and then mineral acid such as hydrochloric acid, followed by separation to an oil layer and a water layer. In this case, it is preferred to adjust pH value of the water layer to a value of from 6 to 7 by dropping slowly 5% hydrochloric acid with ice cooling (0° to 5° C.). After the separation, the water layer is extracted several times with an oil-soluble solvent such as methylene chloride, and the extracts are combined, dehydrated with a dehydrating agent such as anhydrous magnesium sulfate, and the solvent for extraction is distilled off to obtain a chalcone derivative having tetrahydropyranyloxy group of a color of from yellow to brown.

The chalcone derivatives having one or more tetrahydropyranyloxy groups can be converted into hydroxychalcone derivatives by decomposition with water or alcohols to unprotect the tetrahydropyranyloxy group(s). For example, in the case of 2'-hydroxy-4,4'-bis(tetrahydropyranyloxy)chalcone (compound (II-3) above) obtained as described above, 4,2',4'-trihydroxychalcone can be obtained.

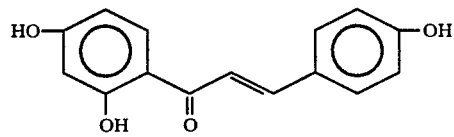

The removal of the protective group is carried out in the presence of an acid catalyst. As for the acid catalyst, there can be used, for example, p-toluenesulfonic acid, formic acid, acetic acid, hydrochloric acid, sulfuric acid, and the like. The solvent which can be used preferably includes water, lower alcohols such as methanol, ethanol, propanol, and the like, and mixtures thereof. Water is added to the resulting hydrolysate to crystalize the reaction product or the reaction product is extracted with an organic solvent such as ethyl acetate to obtain hydroxychalcone.

In this way, various hydroxychalcones can be obtained through the chalcone derivatives having at least one tetrahydropyranyloxy group according to the present invention. Concrete examples thereof are shown in Table 1 below.

In Table 1, "—OH" represents a hydroxyl group, "THPO" a tetrahydropyranyloxy group, and "Me" a methyl group, and "Kind" indicates the type of general formula under which the chalcone derivatives of the present invention fall.

TABLE 1

| | Chalcone Derivative of Invention | Hydroxychalcone |
|---|---|---|
| Kind | Chemical Structure | Chemical Structure |
| I-1 | 3,4,3'-Tris(THPO)chalcone | 3,4,3'-Tri(OH)chalcone |
| I-2 | 3,4,4'-Tris(THPO)chalcone | 3,4,4'-Tri(OH)chalcone |
| II-1 | 2'-OH-3,4-Bis(THPO)chalcone | 3,4,2'-Tri(OH)chalcone |
| II-2 | 2'-OH-4'-(THPO)chalcone | 2',4'-Di(OH)chalcone |
| II-3 | 2'-OH-4,4'-Bis(THPO)chalcone | 4,2',4'-Tri(OH)chalcone |
| II-4 | 2'-OH-3,4,4'-Tris(THPO)chalcone | 3,4,2',4'-Tetra(OH)chalcone |
| II-5 | 2'-OH-4,4'-Bis(THPO)-3-OMe-chalcon | 4,2',4'-Tri(OH)-3-OMe-chalcone |
| II-6 | 2'-OH-3,4'-Bis(THPO)-4-OMe-chalcone | 3,2',4'-Tri(OH)-4-OMe-chalcone |
| II-7 | 2'-OH-2,3,4,4'-Tetrakis(THPO)chalcone | 2,3,4,2',4'-Penta(OH)chalcone |
| II-8 | 2'-OH-3,4,5,4'-Tetrakis(THPO)chalcone | 3,4,5,2',4'-Penta(OH)chalcone |
| II-9 | 2'-OH-4',6'-Bis(THPO)chalcone | 2',4',6'-Tri(OH)chalcone |
| II-10 | 2'-OH-4,4',6'-Tris(THPO)chalcone | 4,2',4',6'-Tetra(OH)chalcone |
| II-11 | 2'-OH-3,4,4',6'-Tetrakis(THPO)chalcone | 3,4,2',4',6'-Penta(OH)chalcone |

Thus, when the compounds described in the right hand column are derived from the corresponding compounds described in the left hand column the respective yields can be improved about 4 times as high as in the cases where the former compounds are prepared directly from acetophenone compounds and benzaldehyde derivatives. This is because the yield of the reaction in which hydroxyl groups of acetophenone and benzaldehyde are substituted with tetrahydropyranyloxy groups can be made as high as, for example, 90% or more, and the yield of Claisen condensation products derived from the derivatives after the thus-performed protection of hydroxyl groups by the substitution can also be made as high as, for example, 90% or more. The latter factor is believed to give greater contribution to improvement in the yield of hydroxychalcones.

The process of producing hydroxychalcone derivatives according to the present invention is economically advantageous since the protection reaction of hydroxyl groups for the introduction of tetrahydropyranyl groups can be carried out by using acid catalysts, Claisen condensation reaction by using basic catalysts, and the reaction for the elimination of tetrahydropyranyl groups to unprotect hydroxyl groups by using acid catalysts, and the respective reactions can be performed in generally employed solvents.

The thus-obtained hydroxychalcones as listed in the right hand column in Table 1 are known to have pharmacological activities. For example, the pharmacological activities of the hydroxychalcone compound described in Table 1 under type number II-3 are as described hereinbefore, the corresponding compounds described in the left hand side column are useful as intermediates for producing such hydroxychalcones.

The above-described processes for the production of chalcone derivatives having a hydroxyl group and a tetrahydropyranyloxy group, and for the decomposition of them with water or alcohols can also be applied to those chalcone derivatives starting from acetophenone or its derivatives and benzaldehyde or its derivatives which reactants each have substituents other than hydroxyl groups. As for the other substituents, there can be cited, for example, a nitro group, an amino group, a halogen atom, an alkyl group, an alkenyl group, an aryl group, an aryloxy group, and the like. The chalcone derivatives may have one or more of these substituents.

EXAMPLES

The present invention will be explained in greater detail with reference to the following examples. However, the present invention should not be construed as being limited thereto.

EXAMPLE 1

(1) Protection of Hydroxyl Group of Hydroxyacetophenone

In a suspension of 21.301 g (140 mmol) of 2,4-dihydroxyacetophenone and 1.205 g (7.00 mmol) of pyridinium p-toluenesulfonate in 64 ml of methylene chloride was added slowly and dropwise 17.665 g (210.0 mmol) of 2,3-dihydropyran at a temperature of from 20° to 25° C.

After 2 hour agitation, 8 g of sodium bicarbonate was added to the reaction mixture, followed by agitation for 2.5 hours. After filtering out sodium bicarbonate, the filtrate was concentrated under reduced pressure to give 35.544 g of 2-hydroxy-4-tetrahydropyranyloxyacetophenone as oily product. The product was obtained stoichiometrically.

The reaction scheme was the same as that described in the above description.

The identification data of the substance thus obtained are as follows.

1) IR (KBr tablet) (cm$^{-1}$) 3450(OH), 2850(C—H), 1620(C=O), 1500, 1425, 1360(aromatic ring).

2) NMR (d$_6$-chloroform) $\delta = 1.5 \sim 2.0$(m, 6H, tetrahydropyranyl group), $3.5 \sim 3.9$(m, 2H, tetrahydropyranyl group), $5.4 \sim 5.5$(dd, 1H, tetrahydropyranyl group), 2.5 (s, 3H, CH), $6.4 \sim 7.6$(m, 3H, aromatic ring).

(2) Protection of Hydroxyl Groups of Hydroxybenzaldehyde

In a suspension of 17.097 g (140 mmol) of 4-hydroxybenzaldehyde and 1.205 g (7.00 mmol) of pyridinium p-toluenesulfonate in 64 ml of methylene chloride was added slowly and dropwise 17.665 g (210.0 mmol) of 2,3-dihydropyran at a temperature of from 20° to 25° C.

After 3 hour agitation, 8 g of sodium bicarbonate was added to the reaction mixture, followed by agitation for 2.5 hours. After filtering out sodium bicarbonate, the filtrate was concentrated under reduced pressure to give 31.496 g of 4-tetrahydropyranyloxybenzaldehyde as oily product. The product was obtained stoichiometrically.

The reaction scheme was the same as that described in the above description.

The identification data of the substance thus obtained are as follows.

1) IR (KBr tablet) (cm$^{-1}$) 3250(COH), 2950(C—H), 1690(C=O), 1600, 1590, 1500 (aromatic ring).

2) NMR (d$_6$-acetone) $\delta = 1.5 \sim 2.0$(m,6H, tetrahydropyranyl group), $3.4 \sim 4.0$(m, 2H, tetrahydropyranyl group), $5.5 \sim 5.6$(dd, 1H, tetrahydropyranyl group), $7.1 \sim 7.9$ (m, 4H, aromatic ring), 9.9 (s, 1H, aldehyde group).

(3) Claisen Condensation Reaction

In 210 ml of methanol were dissolved 35.544 g of 2-hydroxy-4-tetrahydropyranyloxyacetophenone obtained in (1) above, 31.496 g of 4-tetrahydropyranyloxybenzaldehyde obtained in (2) above, and 44.168 g (140 mmol) of barium hydroxide octahydrate, and the solution was agitated at 40° C. for 9 hours. After cooling, 210 ml of methylene chloride was added slowly and then under ice cooling, hydrochloric acid was added slowly and dropwise at a temperature of from 0° to 5° C. to adjust the water layer to pH 6 to 7.

After separation, the water layer was further extracted with methylene chloride. The methylene chloride layers were combined and dried over anhydrous magnesium sulfate. Distillation off of methylene chloride afforded 62.320 g of 2'-hydroxy-4,4'-bis(tetrahydropyranyloxy)chalcone as brown oily product having purity of 77.1% and yield of 80.8%.

The reaction scheme was the same as that described in the above description.

The identification data of the substance thus obtained are as follows.

1) Melting point: 134° to 135° C.

2) IR (KBr tablet) (cm$^{-1}$) 3400(OH), 2950(C—H), 1630(C=O), 1600, 1560, 1500 (aromatic ring), 1230, 1110.

3) NMR (d$_6$-chloroform) $\delta = 1.5 \sim 2.1$(m,12H, tetrahydropyranyl group), $3.5 \sim 4.0$(m, 4H, tetrahydropyranyl group), 5.5 (dd, 2H, tetrahydropyranyl group), $6.5 \sim 7.9$ (m, 9H, chalcone skeleton), 13.3 (s, 1H, OH).

(4) Formation of Hydroxychalcone

A mixture of 4,000 g of crude 2'-hydroxy-4,4'-bis(tetrahydropyranyloxy)chalcone (purity: 79.4%), 64 mg of p-toluenesulfonic acid and 12 ml of methanol was agitated at room temperature for 2 hours. The mixture was poured into 120 ml of water, and crystals which formed were filtered and washed with 250 ml of water. The crystals obtained were dried to obtain 1.836 g of 4,2',4'-trihydroxychalcone having purity of 79.4% and yield of 77.4%.

The identification data of the substance thus obtained are as follows.

1) Melting point: 201° to 202.5° C.

2) IR (KBr tablet) (cm$^{-1}$) 3400, 1625(C=O), 1600, 1580, 1540, 1505 (aromatic ring), 1440, 1340, 1220, 1140, 1010.

3) NMR (d$_6$-DMSO) $\delta = 6.3 \sim 7.8$(m,7H, aromatic ring), 7.8(d, 1H, CO—CH=C J=8 Hz), 8.2(d, 1H, C=CH—Ar J=8 Hz).

4) UV absorption spectrum $\lambda_{max}^{methanol} = 368$ nm.

EXAMPLES 2 TO 13

Chalcone derivatives and hydroxychalcones of Examples 2 to 13 were produced in analogous methods to (1) to (4) in Example 1 except that compounds shown in Table 2 below were used instead of the acetophenone derivative used in (1) above and the benzaldehyde derivatives in (2) above. The yields of the compounds were measured and the results obtained are shown in corresponding column in Table 2 below.

The chalcone derivatives obtained in analogous method to that described in (3) in Example 1 are indicated by reference numerals of the corresponding compounds described in the description, and the hydroxychalcones are those which correspond to such reference numerals. "APH" and "BAD" indicate acetophenone and benzaldehyde, respectively. Other notes are the same as for Table 1.

Identification data for chalcone derivatives and hydroxychalcones are shown after Table 2 below.

COMPARATIVE EXAMPLE 1

The procedures in Example 1 were repeated except that the acetophenone derivative (1) above and the benzaldehyde derivative (2) above were condensed in an aqueous 15% potassium solution at 70° C. for 35 hours to produce hydroxychalcone corresponding to the compound II-3 in Table 1. Purity: 18.9%. Yield: 22.1%.

TABLE 2

| Example | Acetophenone Derivative | Benzaldehyde Derivative | Claisen Condensation Kind | Product Yield | Yield of Hydroxychalcone For (3) | For (1) and (2) |
|---|---|---|---|---|---|---|
| 1 | 2,4-Di-(OH)-APH | 4-(OH)-BAD | II-3 | 80.0 | 99.9 | 80.7 |
| 2 | 3-OH-APH | 3,4-Di-(OH)-BAD | I-1 | 80.2 | 98.2 | 78.8 |
| 3 | 4-OH-APH | 3,4-Di-(OH)-BAD | I-2 | 78.0 | 99.0 | 77.2 |
| 4 | 2-OH-APH | 3,4-Di-(OH)-BAD | II-1 | 77.2 | 97.8 | 75.5 |
| 5 | 2,4-Di-(OH)-APH | BAD | II-2 | 75.3 | 98.1 | 73.9 |
| 6 | 2,4-Di-(OH)-APH | 3,4-Di-(OH)-BAD | II-4 | 75.0 | 98.3 | 73.7 |
| 7 | 2,4-Di(OH)-APH | 4-OH-3-OMe-BAD | II-5 | 82.0 | 99.5 | 81.6 |
| 8 | 2,4-Di-(OH)-APH | 3-OH-4-OMe-BAD | II-6 | 82.0 | 99.1 | 81.3 |
| 9 | 2,4-Di-(OH)-APH | 2,3,4-Tri-(OH)-BAD | II-7 | 76.0 | 93.2 | 70.8 |
| 10 | 2,4-Di-(OH)-APH | 3,4,5-Tri-(OH)-BAD | II-8 | 75.2 | 94.7 | 71.2 |

TABLE 2-continued

| Example | Acetophenone Derivative | Benzaldehyde Derivative | Claisen Condensation | | Yield of Hydroxychalcone | |
|---|---|---|---|---|---|---|
| | | | Kind | Product Yield | For (3) | For (1) and (2) |
| 11 | 2,4,6-Tri-(OH)-APH | BAD | II-9 | 79.6 | 98.0 | 78.0 |
| 12 | 2,4,6-Tri-(OH)-APH | 4-OH-BAD | II-10 | 72.1 | 97.6 | 70.4 |
| 13 | 2,4,6-Tri-(OH)-APH | 3,4-Di-(OH)-BAD | II-11 | 75.4 | 96.4 | 72.7 |
| C.E. | 2,4-Di-(OH)-APH | 4-(OH)-BAD | II-3 | 22.1 | — | 22.1 |

IDENTIFICATION DATA

Hydroxychalcone according to Example 2

(3,4,3'-Trihydroxychalcone)

(1) Melting point: 186° to 191° C.
(2) IR (KBr tablet) (cm$^{-1}$) 3400 (OH), 1560 (C=O), 1640, 1600, 1520 (aromatic ring), 1450, 1350, 1280, 1160, 1030, 790.
(3) NMR (d$_6$-acetone) $\delta = 6.8 \sim 7.7$ (m, 9H, chalcone skeleton), 8.4 (br, 3H, OH).
(4) UV absorption spectrum $\lambda_{max}{}^{methanol} = 362$ nm.

Hydroxychalcone according to Example 3

(3,4,4'-Trihydroxychalcone)

(1) Melting point: 210.5° to 212.5° C.
(2) IR (KBr tablet) (cm$^{-1}$) 3400 (OH), 1590 (C=O), 1640, 1560, 1520 (aromatic ring), 1440, 1370, 1220, 1160, 1030, 790.
(3) NMR (d$_6$-acetone) $\delta = 6.7 \sim 8.1$ (m, 9H, chalcone skeleton), 8.0 (br, 1H, OH), 8.3 (br, 1H, OH), 9.0 (br, 1H, OH).
(4) UV absorption spectrum $\lambda_{max}{}^{methanol} = 361$ nm.

Hydroxychalcone according to Example 4

(3,4,2'-Trihydroxychalcone)

(1) Melting point: 177.5° to 178.5° C.
(2) IR (KBr tablet) (cm$^{-1}$) 3350 (OH), 1580 (C=O), 1630, 1520, 1485 (aromatic ring), 1440, 1280, 1200, 1150.
(3) NMR (d$_6$-acetone) $\delta = 6.8 \sim 8.3$ (m, 9H, chalcone skeleton), 8.2 (br, 1H, OH), 8.5 (br, 1H, OH), 13.) (s, 1H, 2'—OH).
(4) UV absorption spectrum $\lambda_{max}{}^{methanol} = 382$ nm.

Chalcone Derivative According to Example 5 (Claisen Condensation Product (2'-Hydroxy-4'-tetrahydropyranyloxychalcone)

$\delta = 1.6 \sim 2.1$ (m, 6H, tetrahydropyranyl group), $3.6 \sim 3.9$ (m, 2H, tetrahydropyranyl group), 5.5 (s, 1H, tetrahydropyranyl group), $6.5 \sim 8.0$ (m, 10H, aromatic ring), 13.3 (s, 1H, 2'—OH).

Hydroxychalcone According to Example 5

(2,4'-Diihydroxychalcone)

(1) Melting point: 144.5° to 145.5° C.
(2) IR (KBr tablet) (cm$^{-1}$) 3250 (OH), 1625 (C=O), 1635, 1590, 1490 (aromatic ring), 1360, 1300, 1220, 1140.
(3) NMR (d$_6$-DMSO+CDCl$_3$) $\delta = 6.5 \sim 7.9$ (m, 10H, chalcone skeleton), 9.8 (br, 1H, OH), 13.4 (s, 1H, 2'—OH).

Hydroxychalcone According to Example 6

(3,4,2',4'-Tetrahydroxychalcone)

(1) Melting point: 223.5° to 225° C.
(2) IR (KBr tablet) (cm$^{-1}$) 3300 (OH), 1635 (C=O), 1635, 1590, 1550, 1510 (aromatic ring), 1450, 1340, 1230, 1145, 1120, 1025, 970.
(3) NMR (d$_6$-acetone) $\delta = 6.3 \sim 7.8$ (m, 8H, chalcone skeleton), 9.1 (br, 3H, OH), 13.5 (s, 1H, 2'—OH).
(4) UV absorption spectrum $\lambda_{max}{}^{methanol} = 380$ nm.

Hydroxychalcone According to Example 7

(4,2',4'-Trihydroxy-3-methoxychalcone)

(1) Melting point: 203.5° to 207° C.
(2) IR (KBr tablet) (cm$^{-1}$) 3200 (OH), 1580 (C=O), 1620, 1540, 1490, 1460 (aromatic ring), 1360, 1270, 1240, 1200, 1025, 965.
(3) NMR (d$_6$-acetone)
$\delta = 4.0$ (s, 3H, OCH$_3$), $6.3 \sim 7.8$ (m, 6H, aromatic ring0, 6.9 (d, 1H, CO—CH=C J=6.9 Hz), 8.1 (d, 1H, C=CH—Ar J=6.9 Hz), 8.2 (br, 1H, OH), 9.5 (br, 1H, OH), 13.6 (s, 1H, 2'—OH).
(4) UV absorption spectrum $\lambda_{max}{}^{methanol} = 369$ nm.

Hydroxychalcone According to Example 8

(3,2',4'-Trihydroxy-4-methoxychalcone)

(1) Melting point: 189° to 191° C.
(2) IR (KBr tablet) (cm$^{-1}$) 3350 (OH), 1570 (C=O), 1635, 1590, 1505, 1440 (aromatic ring), 1350, 1305, 1260, 1130, 1020, 980.
(3) NMR (d$_6$-acetone) $\delta = 3.9$ (s, 3H, OCH$_3$), $6.3 \sim 7.8$ (m, 6H, aromatic ring), 7.0 (d, 1H, CO—CH=C J=6.9 Hz), 8.1 (d, 1H, C=CH—Ar J=6.9 Hz), 7.8 (br, 1H, OH), 9.4 (br, 1H, OH), 13.6 (s, 1H, 2'—OH).
(4) UV absorption spectrum $\lambda_{max}{}^{methanol} = 366$ nm.

Hydroxychalcone According to Example 9

(2,3,4,2',4'-Pentahydroxychalcone)

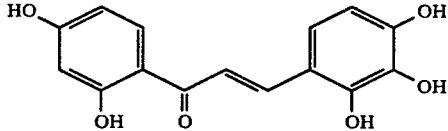

(1) Yellowish orange crystal.
(2) Melting point: 165° to 170° C.
(3) IR (KBr tablet) (cm$^{-1}$) 3400, 3150 (OH), 1620 (C=O), 1600, 1560, 1510 (aromatic ring), 1350, 1230, 1070, 980, 790.
(4) NMR (d$_6$-DMSO) $\delta = 6.3 \sim 8.2$ (m, 7H, chalcone skeleton), 9.6 (br, 4H, OH), 13.5 (s, 1H, OH).
(5) UV absorption spectrum $\lambda_{max}{}^{ethanol} = 395$ nm.

Hydroxychalcone According to Example 11

(2',4',6'-Trihydroxychalcone)

(1) Melting point: 178° to 180° C.

(2) IR (KBr tablet) (cm$^{-1}$) 3300 (OH), 1620 (C=O), 1550, 1500, 1445 (aromatic ring), 1400, 1340, 1280, 1220, 1075.

(3) NMR (d$_6$-DMSO) δ=5.9 (s, 2H, aromatic ring), 7.4~7.7 (m, 5H, aromatic ring), 7.7 (d, 1H, CO—CH=C J=14.5 Hz), 8.1 (d, 1H, C=CH—Ar J—14.5 Hz), 10.5 (s, 1H, OH), 12.5 (s, 1H, 2'—OH).

Hydroxychalcone According to Example 12

(4,2',4',6'-Tetrahydroxychalcone)

(1) Melting point: 200° to 201° C.

(2) IR (KBr tablet) (cm$^{-1}$) 3250 (OH), 1620 (C=O), 1580, 1545, 1500 (aromatic ring), 1340, 1290, 1210, 1160, 1020.

(3) NMR (d$_6$-DMSO) δ=5.8 (s, 2H, aromatic ring), 6.8 (d, 2H, aromatic ring J=9.4 Hz), 7.1 (d, 1H, CO—CH=C J=12.9 Hz), 7.5 (d, 2H, aromatic ring), 8.0 (d, 1H, C=CH—Ar J=12.9 Hz), 10.1 (br, 1H, OH), 10.4 (br, 1H, OH), 12.5 (br, 2H, 2'— and 6'—OH).

Hydroxychalcone According to Example 13

(3,4,2',4',6'-Pentahydroxychalcone)

(1) Melting point: 248.5° to 251.5° C.

(2) IR (KBr tablet) (cm$^{-1}$) 3250 (OH), 1600 (C=O), 1550, 1500 (aromatic ring), 1320, 1270, 1200, 1020, 970.

(3) NMR (d$_6$-acetone) δ=5.8 (s, 2H, aromatic ring), 6.8~7.1 (m, 3H, aromatic ring), 7.6 (d, 1H, CO—CH=C J=12.9 Hz), 7.9 (d, 1H, C=CH—Ar J=12.9 Hz), 9.2 (s, 1H, OH), 9.6 (s, 1H, OH), 10.4 (s, 1H, OH), 12.5 (s, 2H, 2'— and 6'—OH).

EXAMPLE 14

(1) Simultaneous Protection of Respective Hydroxyl Groups of Hydroxyacetophenone and Hydroxybenzaldehyde In a suspension of 21.301 g (140 mmol) of 2,4-dihydroxyacetophenone, 17.097 g (140 mmol) of 4-hydroxybenzaldehyde and 1.205 g (7.00 mmol) of pyridinium p-toluenesulfonate in 154 ml of methylene chloride was added slowly and dropwise 35.331 g (420 mmol) of 2,3-dihydropyran at a temperature of from 20° to 25° C.

After 3 hour agitation, 8 g of sodium bicarbonate was added to the reaction mixture, followed by agitation for 2.5 hours. After filtering out sodium bicarbonate, the filtrate was concentrated under reduced pressure to give 71.424 g of a mixture of 20hydroxy-4-tetrahydropyranyloxyacetophenone and 4-tetrahydropyranyloxybenzaldehyde as pale orange oily product. The product was obtained stoichiometrically.

The identification data of the mixture thus obtained are substantially the same as the data of mixture of the products (1) and (2) obtained in Example 1.

(2) Claisen Condensation Reaction

In 210 ml of methanol were dissolved 71.424 g of the mixture of 2-hydroxy-4-tetrahydropyranyloxyacetophenone and 4-tetrahydropyranyloxybenzaldehyde obtained in (1) above and 44.168 g (140 mmol) of barium hydroxide octahydrate, and the solution was agitated at 40° C. for 9 hours. After cooling, 210 ml of methylene chloride was added and then under ice cooling, hydrochloric acid was added slowly and dropwise at a temperature of from 0° to 5° C. to adjust the water layer to pH 6 to 7.

After separation, the water layer was further extracted with methylene chloride. The methylene chloride layers were combined and dried over anhydrous magnesium sulfate. Distillation off of methylene chloride afforded 67.064 g of 2'-hydroxy-4,4'-bis(tetrahydropyranyloxy)chalcone as brown oily product having purity of 79.4% and yield of 89.6%.

The identification data of the substance thus obtained were substantially the same as those of the product obtained in (3) in Example 1.

(3) Formation of Hydroxychalcone

To a mixture of 4,000 g of crude 2'-hydroxy-4,4'-bis(-tetrahydropyranyloxy)chalcone (purity: 79.4%) and 13 ml of a mixed solvent of methylene chloride:methanol:-water (4:4:1) was added 0.18 g of p-toluenesulfonic acid monohydrate, and the resulting mixture was agitated ar room temperature for 2 hours. The mixture was poured into 120 ml of water, and extracted with ethyl acetate. Distillation off of ethyl acetate afforded 2.770 g of 4,2',4'-trihydroxychalcone, having purity of 69.1% and yield of 99.9%.

The identification data of the substance thus obtained were substantially the same as those of the product obtained in (4) in Example 1.

What is claimed is:

1. A hydroxychalcone derivative represented by general formula (I)

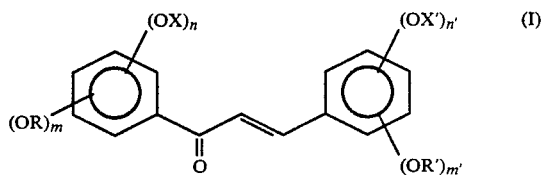

wherein X and X' each represent 2-tetrahydropyranyl, R and R', which are the same or different, each represent and alkyl group or a hydrogen atom, n and n' each is an integer of from 0 to 3, m and m' are each integers of from 0 to 3, provided that n+n' is 1 or more, and than n+m is an integer of from 1 to 3 and n'+m is an integer of from 1 to 3.

2. A hydroxychalcone derivative as claimed in claim 1, wherein n and n' each are an integer of from 1 to 3, and m and m' each are 0.

3. A hydroxychalcone derivative as claimed in claim 1, wherein said derivative is represented by formula:

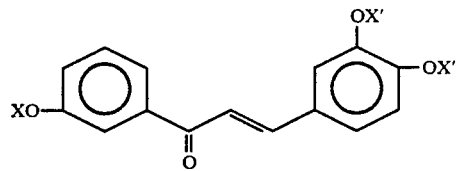

wherein X and X' each represent 2-tetrahydropyranyl.

4. A hydroxychalcone derivative as claimed in claim 1, wherein said derivative is represented by formula:

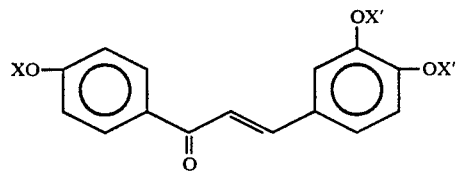

wherein X and X' each represent 2-tetrahydropyranyl.

5. A chalcone derivative represented by general formula (II) below.

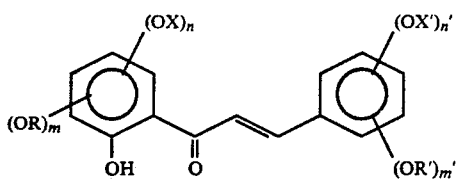

wherein X and X' each represent 2-tetrahydropyranyl, R and R', which are the same or different, each represent an alkyl group or a hydrogen atom, n is an integer of from 0 to 2, n' is an integer of from 0 to 3, m is an integer of from 0 to 2, and m' is an integer of from 0 to 3, provided that n+n' is 1 or more, and that n+m is an integer of from 0 to 3 and n'+m' is an integer of from 1 to 3.

6. A chalcone derivative as claimed in claim 5, wherein m is 0.

7. A chalcone derivative as claimed in claim 5, wherein m and m' each are 0.

8. A chalcone derivative as claimed in claim 5, wherein said derivative is represented by formula:

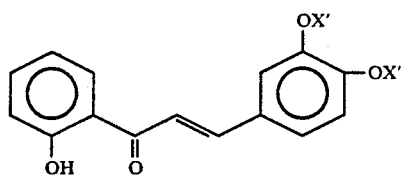

wherein X' has the same meaning as defined in claim 5.

9. A chalcone derivative as claimed in claim 5, wherein said derivative is represented by formula:

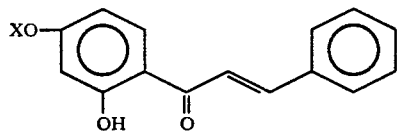

wherein X has the same meaning as defined in claim 5.

10. A chalcone derivative as claimed in claim 5, wherein said derivative is represented by formula:

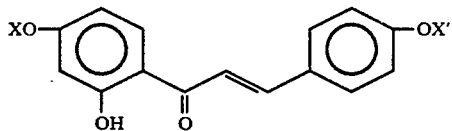

wherein X and X' have the same meanings as defined in claim 5.

11. A chalcone derivative as claimed in claim 5, wherein said derivative is represented by formula:

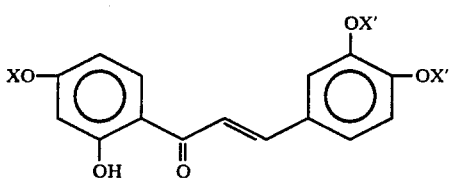

wherein X and X' have the same meanings as defined in claim 5.

12. A chalcone derivative as claimed in claim 5, wherein said derivative is represented by formula:

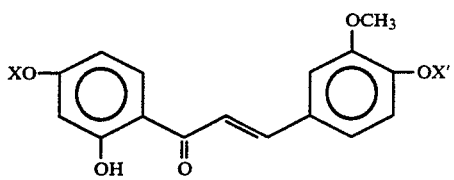

wherein X and X' have the same meanings as defined in claim 5.

13. A chalcone derivative as claimed in claim 8, wherein said derivative is represented by formula:

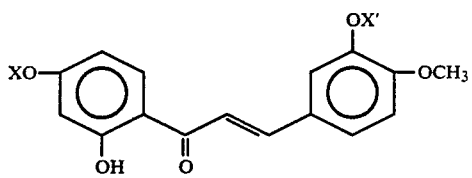

wherein X and X' have the same meanings as defined in claim 5.

14. A chalcone derivative as claimed in claim 5, wherein said derivative is represented by formula:

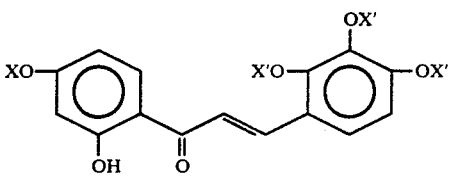

wherein X and X' have the same meanings as defined in claim 5.

15. A chalcone derivative as claimed in claim 5, wherein said derivative is represented by formula:

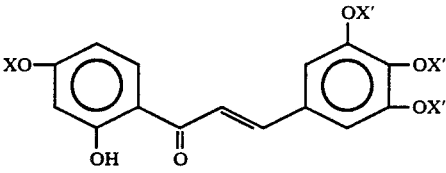

wherein X and X' have the same meanings as defined in claim 5.

16. A chalcone derivative as claimed in claim 5, wherein said derivative is represented by formula:

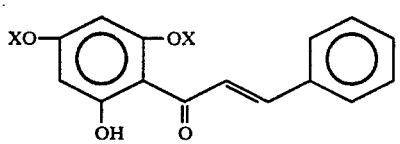

wherein X has the same meaning as defined in claim 5.

17. A chalcone derivative as claimed in claim 5, wherein said derivative is represented by formula:

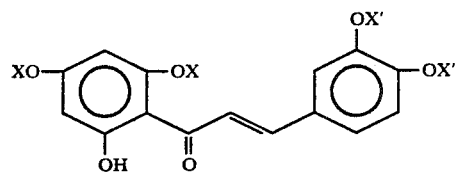
wherein X and X' have the same meanings as defined in claim 5.
18. A chalcone derivative as claimed in claim 5, wherein said derivative is represented by formula:
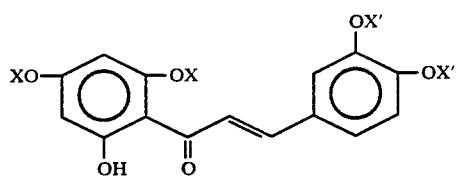
wherein X and X' have the same meanings as defined in claim 5.
* * * * *